United States Patent
Binay

(10) Patent No.: US 9,718,833 B2
(45) Date of Patent: Aug. 1, 2017

(54) TRITOQUALINE HYDROCHLORIDE IN CRYSTALLINE FORM AND A PROCESS FOR OBTAINING SAME

(71) Applicant: Patrice Binay, Couchey (FR)

(72) Inventor: Patrice Binay, Couchey (FR)

(*) Notice: Subject to any disclaimer, the term of this patent is extended or adjusted under 35 U.S.C. 154(b) by 0 days.

(21) Appl. No.: 15/104,006

(22) PCT Filed: Dec. 29, 2014

(86) PCT No.: PCT/FR2014/000306
§ 371 (c)(1),
(2) Date: Jun. 13, 2016

(87) PCT Pub. No.: WO2015/101727
PCT Pub. Date: Jul. 9, 2015

(65) Prior Publication Data
US 2016/0318945 A1 Nov. 3, 2016

(30) Foreign Application Priority Data

Dec. 30, 2013 (FR) .................................... 13 03107

(51) Int. Cl.
*C07D 491/056* (2006.01)

(52) U.S. Cl.
CPC ...... *C07D 491/056* (2013.01); *C07B 2200/13* (2013.01)

(58) Field of Classification Search
CPC .................................................. C07D 491/056
USPC ........................................................... 546/90
See application file for complete search history.

(56) References Cited

U.S. PATENT DOCUMENTS 8,207,292 B2 * 6/2012 Nicolaou ............. A61K 31/341
530/206
2016/0251367 A1 * 9/2016 Terrasse ............. C07D 491/056

* cited by examiner

*Primary Examiner* — Patricia L Morris
(74) *Attorney, Agent, or Firm* — Oliff PLC

(57) ABSTRACT

A crystalline form of tritoqualine hydrochloride and also a process for obtaining same. The process for obtaining tritoqualine hydrochloride is made of dissolving tritoqualine base in an alcohol, in particular a lower aliphatic alcohol, such as ethanol, in the presence of hydrochloric acid until a solution in the supersaturated state is obtained. Through successive additions of ether, in particular of ethyl ether, the tritoqualine hydrochloride will subsequently be able to crystallize. The product can be applied to the preparation of pharmaceutical formulations.

7 Claims, 2 Drawing Sheets

TRITOQUALINE HYDROCHLORIDE IN CRYSTALLINE FORM AND A PROCESS FOR OBTAINING SAME

BACKGROUND

The present invention relates to a crystallized form of tritoqualine hydrochloride as well as to a method for obtaining same.

Tritoqualine, for which the chemical name is 7-amino-4,5,6-triethoxy-3-(4-methoxy-6-methyl-7,8-dihydro-5H-[1,3]dioxolo[4,5-g]isoquinoline-5-yl)-3H-isobenzofuran-1-one is a molecule known for its assumed antihistaminic action; in particular this is an enzymatic inhibitor of L-histidine decarboxylase. It has been demonstrated recently that this activity was very low; on the other hand its activity on the H4 receptor has raised strong interest for a few years. In particular, this molecule was widely studied in the field of digestive inflammatory diseases and more particularly gastric and esophageal diseases.

It was also found that tritoqualine was of interest in the treatment of acute leukemias and in that of cystic fibrosis, chronic obstructive pulmonary disease (COPD) and exacerbation of asthma.

These various applications of tritoqualine have been the subject of many patents.

However, the optimum use of tritoqualine encountered various problems related to the intrinsic physicochemical properties of the molecule, and in particular its very low solubility (100 ppm in water at room temperature).

Various methods were used for increasing the solubility and therefore the bioavailability of tritoqualine, for example by passing from the stage of tritoqualine hydrochloride formed in situ by addition of hydrochloric acid to tritoqualine in solution. The latter has a half lifetime of a few hours in an aqueous solution. The molecule is split at the 2 asymmetrical carbon atoms between the isoquinoline ring (cotarnine) and the phthalic ring.

In spite of many tests, it has never been possible to isolate tritoqualine hydrochloride in a crystallized form, which would have given the possibility of greater reproducibility of the clinical studies conducted with this molecule and better control of the action of tritoqualine upon its administration to patients.

SUMMARY

The present invention specifically relates to tritoqualine hydrochloride in a crystallized form as well as a method for obtaining this crystallized form.

DETAILED DESCRIPTION

Figure 1:
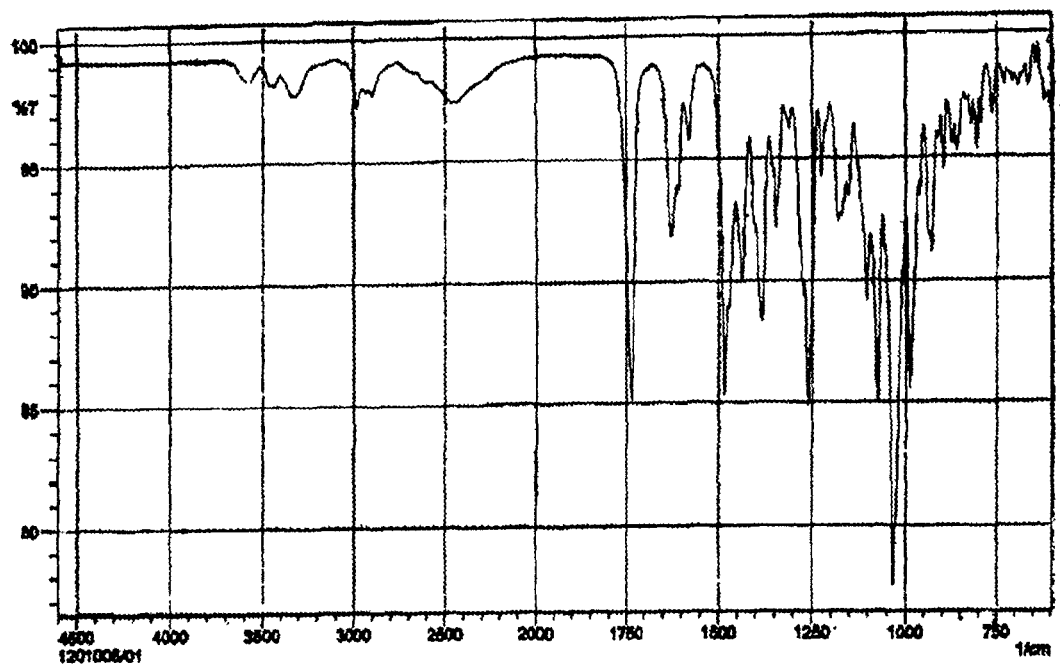
FIG. 1 is an IR spectrum of tritoqualine hydrochloride.

A preferential method for synthesis of the crystallized tritoqualine hydrochloride will now be described, the reaction being overall the following:

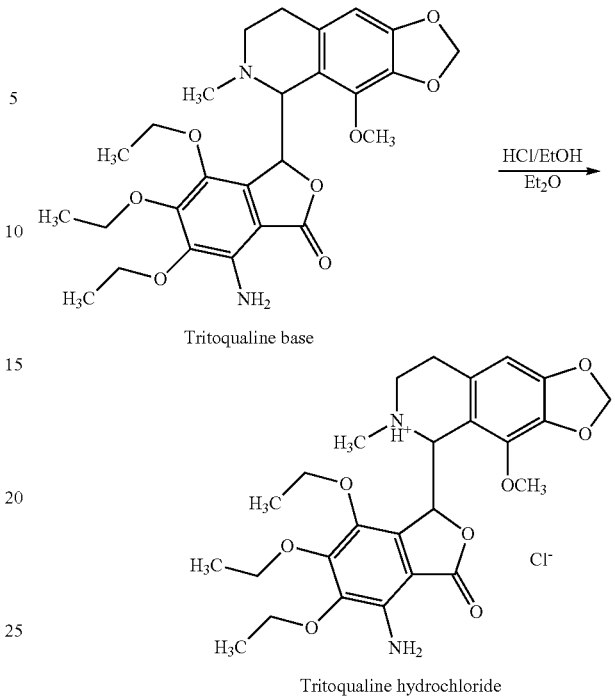

Tritoqualine base

Tritoqualine hydrochloride

An operating procedure will now be described in more detail.

In an Erlenmeyer of 500 ml provided with a magnetized bar and magnetic stirring, introduced by means of a spatula 30 g of tritoqualine base into 45 ml of absolute ethanol (1.5 volume) at room temperature, and then rapidly add an with rapid stirring, 6 ml of 37% hydrochloric acid (i.e. 1 molar equivalent).

As soon as the end of the addition of hydrochloric acid, the tritoqualine base still in suspension, is gradually dissolved in the ethanol in a few minutes. Although this solution is highly concentrated (supersaturated solution), the tritoqualine hydrochloride remains in solution because of an under-cooling phenomenon. Gradually add about 120 ml of ethyl ether (4 volumes) by successive fractions from 15 to 20 ml. Each addition causes cloudiness of the solution by the occurrence of a second phase. This opalescence disappears after a few tens of seconds of stirring at room temperature and the solution again becomes clear and translucent. Continue the addition of small ethyl ether fractions. When the accumulated additions of ether are of the order of 3 volumes, the opalescence becomes persisting, stop the addition of ether at a specific moment and maintain the stirring for 15 min at room temperature; tritoqualine hydrochloride gradually precipitates during this phase. Add the remainder of ether (up to 4 volumes) in order to enhance the crystallization yield. Maintain the stirring for an additional half-hour. The stirring should be sufficient so as to give the possibility of obtaining a suspension with a homogenous aspect.

If the stirring is too weak, the tritoqualine hydrochloride decants in the bottom of the Erlenmeyer; on the contrary, if the addition of the ether is too rapid (i.e. without waiting for disappearance of the opalescence between two additions of ether, then the tritoqualine hydrochloride is of very poor quality: it does not precipitate suitably and leads to a more or less amorphous and tacky product (a sort of colorless and viscous gel filled with solvent) or a very tacky mixture of crystals and of amorphous gel.

When the crystallization operation is conducted suitably according to the method above, the obtained suspension is filtered under reduced pressure on sintered glass no. 3 or 4; filtration is rapid and the cake does not block the filter.

The cake is of a very white aspect and the mother liquors are colorless to slightly yellow. It is nevertheless preferable to proceed with piston washing of the cake with 20 ml (2 volumes) of additional ethyl ether.

The filtration juices and the washing juices are collected together and stirred for 1 further hour while gradually cooling the whole to 5° C. A second jet again precipitates. The latter is filtered and then treated in the same way as the first crystallization jet.

Mass of the $1^{st}$ jet after drying: 28.0 g i.e. a yield of 87%
Mass of the $2^{nd}$ jet after drying: 3.6 g
i.e. a total of 31.6 g of crystallized tritoqualine hydrochloride.

Expected theoretical mass: 32.3 g/overall yield=98%.

The comparative physico-chemical properties of tritoqualine base and of the crystallized tritoqualine hydrochloride are gathered in the table below.

| Tritoqualine | MP ° C. | Solubility | | Stability to light |
|---|---|---|---|---|
| | | in water | in ethanol | |
| Base $C_{26}HG_{32}N_2O_8$ molar mass: 500.5 | 184° C. | 150 ppm (practically insoluble and hydrophobic) | 2.5 g/l at 20° C., 50 g/l with refluxed with ethanol | Becomes gradually yellow after a few days of exposure to natural light |
| Hydrochloride $C_{26}H_{33}ClN_2O_8$ molar mass: 537 | Decomposition at T >170° C. | Hydrophilic and soluble at pH <3, gradually decomposes in an aqueous solution when the temperature increases | >300 g/l at 20° C., decomposes upon refluxed with cotarnine | Stable to natural light for several weeks |

Moreover, tritoqualine hydrochloride is very little soluble or even insoluble in ethers; on the other hand it is soluble in primary alcohols, acetone and methyl ethyl ketone.

Various analyses were conducted in order to establish that the formed product is actually tritoqualine hydrochloride.

Thus, the IR spectrum of tritoqualine hydrochloride illustrated in the graph FIG. 1 actually shows a wide band at 2,400 $cm^{-1}$ characteristic of the ammonium group.

Figure 2:
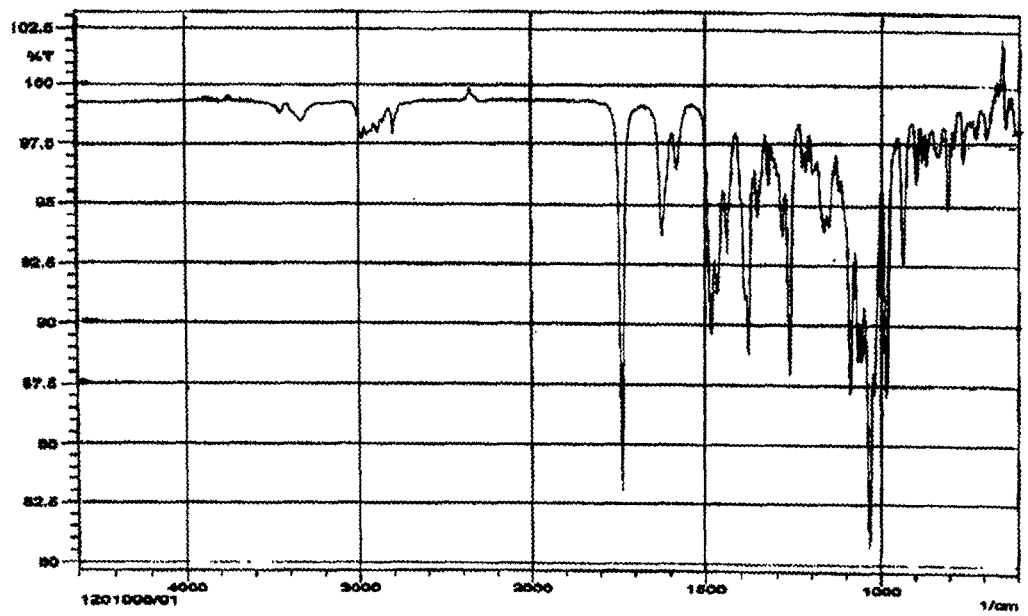
FIG. 2 is an IR spectrum of tritoqualine base.

On the other hand, this band does not appear on the IR spectrum of tritoqualine base illustrated in the FIG. 2.

The $^1H$ and $^{13}C$ NMR spectrum, not shown here, actually confirms that this is actually tritoqualine hydrochloride.

Moreover, dosage of the chloride ions is 6.7% and corresponds to the formation of a monohydrochloride. The synthesis of a dihydrochloride (one on the nitrogen atom of quinoline and a second on the primary amine) was attempted by adding two equivalents of hydrochloric acid. The monohydrochloride is always obtained, identical as the one described earlier.

Finally, it is of interest to note that the tritoqualine hydrochloride has the same profile of impurities as that of the tritoqualine base used for its synthesis.

In the preferential synthesis example described earlier, ethanol is used as a solvent, but other alcohols may be used, in particular lower aliphatic alcohols, for example methanol or isopropanol. Although producing lower yields and a more random crystallization, it was also possible to dissolve the tritoqualine base in the presence of hydrochloric acid in acetone or methyl ethyl ketone, or else further in glycol derivatives such as glyme, also called dimethyl glycol, diglyme, also designated as di(2-methoxyethyl)ether, or diethylene glycol monomethyl ether.

Also, the ethyl ether used during the crystallization of tritoqualine hydrochloride may be replaced with another ether, such as for example tert-butyl methyl ether or tetrahydrofurane.

The thereby obtained tritoqualine hydrochloride is hydrophilic and soluble in an aqueous solution at pH<3.0 as this appears in the table above; this solubility reinforces the action of tritoqualine in the stomach—the contents of which have a pH of the order of 2 to 3.5—in the treatment of digestive inflammatory diseases. When the aqueous solution attains a pH>3.0, tritoqualine hydrochloride precipitates, but in quite an interesting way, this precipitation occurs in the form of very fine particles, then giving the solution the aspect of a milk and thus substantially increasing the bioavailability of tritoqualine which has its contact surface area considerably increased.

Thus, the importance of a crystallized form of tritoqualine hydrochloride will be better understood which, unlike tritoqualine base which is hydrophobic and practically insoluble, is both hydrophilic and soluble.

Further it appeared quite unexpectedly, that there exists a very great difference in solubility in alcohols and glycols between tritoqualine base and tritoqualine hydrochloride, the latter being much more soluble than tritoqualine base.

This increased solubility of tritoqualine hydrochloride in alcohols and glycols thus gives the possibility of accessing formulations which are inaccessible by another means.

Moreover, tritoqualine hydrochloride is highly stable as this emerges from the table above. This quite unexpected stability as compared with the low stability to light of tritoqualine base gives the possibility of preparing pharmaceutical compositions containing tritoqualine in the form of its hydrochloride for the aforementioned therapeutic uses.

In the operating procedure described earlier, concentrated hydrochloric acid is used; tritoqualine hydrochloride may also be obtained under satisfactory conditions by using hydrochloric acid in gas form injected into the solution.

The invention claimed is:
1. A method for obtaining tritoqualine hydrochloride in crystalline form, wherein the method comprises dissolving tritoqualine base in an alcohol or in a glycol derivative selected from the group consisting of dimethyl glycol, di(2-methoxyethyl)ether, and diethylene glycol monomethyl ether, in the presence of hydrochloric acid until a solution in a supersaturation state is obtained.

2. The method according to claim 1, wherein the alcohol is ethanol.

3. The method according to claim 1, wherein said solution is then subject to a treatment with an ether.

4. The method according to claim 3, wherein said ether is ethyl ether.

5. The method according to claim 3, wherein said treatment is accomplished by successive additions of ether fractions.

6. The method according to claim 5, wherein, before carrying out a new addition of ether, it is awaited that the solution is no longer opalescent.

7. The method according to claim 3, wherein the ether proportion used is of 4 volumes for 1.5 volumes of alcohol or of glycol derivative allowing dissolution of tritoqualine.

\* \* \* \* \*